(12) United States Patent
Park et al.

(10) Patent No.: US 7,171,270 B1
(45) Date of Patent: Jan. 30, 2007

(54) IMPLANTABLE CARDIAC DEVICE TO PROMOTE INTRINSIC RHYTHM TO ALLEVIATE ORTHOSTATIC HYPOTENSION

(75) Inventors: Euljoon Park, Valencia, CA (US); Michael Benser, Valencia, CA (US); Ruth Lyons, Glendale, CA (US)

(73) Assignee: Pacesetter, Inc., Sylmar, CA (US)

( * ) Notice: Subject to any disclaimer, the term of this patent is extended or adjusted under 35 U.S.C. 154(b) by 165 days.

(21) Appl. No.: 10/748,486

(22) Filed: Dec. 29, 2003

(51) Int. Cl.
*A61N 1/00* (2006.01)
(52) U.S. Cl. ....................... 607/17
(58) Field of Classification Search .............. 607/9, 607/17
See application file for complete search history.

(56) References Cited

U.S. PATENT DOCUMENTS

| | | | | |
|---|---|---|---|---|
| 4,846,195 | A * | 7/1989 | Alt ............... | 600/595 |
| 5,476,483 | A | 12/1995 | Bornzin et al. ............... | 607/17 |
| 5,725,562 | A * | 3/1998 | Sheldon ........................ | 607/19 |
| 5,957,957 | A * | 9/1999 | Sheldon ........................ | 607/17 |
| 6,044,297 | A * | 3/2000 | Sheldon et al. ............... | 607/17 |
| 6,104,949 | A * | 8/2000 | Pitts Crick et al. ......... | 600/547 |
| 6,134,471 | A * | 10/2000 | Dauer et al. ................... | 607/17 |
| 6,308,098 | B1 * | 10/2001 | Meyer .......................... | 607/17 |
| 6,351,672 | B1 | 2/2002 | Park et al. ..................... | 607/19 |
| 6,466,821 | B1 * | 10/2002 | Pianca et al. ................. | 607/18 |
| 2002/0004671 | A1 | 1/2002 | Bornzin et al. ............... | 607/9 |
| 2002/0147475 | A1 * | 10/2002 | Scheiner et al. .............. | 607/17 |
| 2002/0147476 | A1 * | 10/2002 | Daum .......................... | 607/17 |
| 2002/0170193 | A1 * | 11/2002 | Townsend et al. ............ | 33/512 |

FOREIGN PATENT DOCUMENTS

EP  1 070 516 A2  6/2000

OTHER PUBLICATIONS

S. Velasco, et al., "Sincopes Disautonómicos. Diagnóstico y Tratamiento", *Revista De Medicina De La Universidad D Navarra*, 1990; vol. XXXIV, No. 4, pp. 209-218.

Michele Brignole, et al., "La Scelta Del Modo Di Stimolazione Nei Soggetti Con Ipersensibilità Seno-Carotidea Cardioinibritice e Mista, Con e Senza Disfunzione Sinusale Associata", *G. Ital. Cardiol.*, 1989; vol. 19, pp. 28-34.

Dr. med. Vokler Schibgilla, "Influence of Artificial Cardiac Pacing on Cardiovascular Regulation of Pacemaker Patients: Significance and Therapeutic Implications", *Medical Clinic II (Cardiology with Teach Hospital of the University of Erlangen-Nuremberg (Director: Prof. Dr. med. K. Bachmann), Habilitation Thesis of the Faculty of Medicine of the Friedrich Alexander University Erlangen-Nuremberg*, 1997; 101 pages.

* cited by examiner

*Primary Examiner*—George Manuel
*Assistant Examiner*—Lenwood Faulcon

(57) ABSTRACT

An implantable cardiac device is programmed to promote intrinsic rhythm of a patient's heart to alleviate orthostatic hypotension. In one implementation, the cardiac device is set in a reduced rate mode while the patient is in a less upright position, such as when resting in a supine position. If the patient is in intrinsic rhythm when transitioning to a more upright position, the cardiac device disables administration of any increased pacing rate for a programmed duration. In this manner, the patient will experience a more natural variation in heart rate during transition from the less upright posture to the more upright posture (e.g., from supine to sitting or standing). On the other hand, if the patient is being paced during the transition, the cardiac device administers an increased base rate or triggers an orthostatic response algorithm.

19 Claims, 3 Drawing Sheets

IMPLANTABLE CARDIAC DEVICE TO PROMOTE INTRINSIC RHYTHM TO ALLEVIATE ORTHOSTATIC HYPOTENSION

TECHNICAL FIELD

The present invention generally relates to implantable cardiac devices, and particularly, to techniques for alleviating orthostatic hypotension.

BACKGROUND

Orthostatic hypotension is experienced when a person sits or stands up following a prolonged rest period in a horizontal or supine position. Orthostasis means upright posture, and hypotension means low blood pressure. During such a change in posture, the cardiovascular system may make rapid adjustments to increase blood pressure and heart rate. When such adjustments are not made, orthostatic hypotension may occur. Orthostatic hypotension is commonly defined as a decrease of at least 20 mm Hg in systolic blood pressure and/or a 10 mm Hg drop in diastolic blood pressure when an individual moves from the horizontal to upright position.

The symptoms of orthostatic hypotension include dizziness, faintness, or lightheadedness that manifest when changing positions from lying to sitting or standing. Other symptoms that often accompany orthostatic hypotension include chest pain, trouble holding urine, impotence, and dry skin from loss of sweating. Some patients with severe orthostatic hypotension are severely incapacitated.

Implantable cardiac stimulation devices, such as pacemakers, have been used to combat orthostatic hypotension. As the use of such devices is still relatively new, there is ongoing research concerning the effectiveness of current pacing therapies on orthostatic hypotension. One research report produced by researchers Shibgilla and colleagues examined changes in blood pressure of pacemaker patients in response to upward tilts of the patients. First, the researchers screened out pacemaker patients whose rhythm upon standing was, with their standard programmed pacemaker settings, intrinsic (only 26% of patients). Next, the patients who were paced upon standing (74%) were subjected to multiple tilts, each with their pacemaker set to various base rates and pacing configuration settings. Perhaps surprisingly, the researchers found that the transient blood pressure drop upon tilt was smallest when patients were set to slower base rates (e.g., VVI 40 bpm, the slowest test base rate setting where patients were in their intrinsic rhythm). All other base rate settings (e.g., 60–90 bpm) in either AAI, VVI, or DDD modes, during which the patients were paced throughout the tilt, yielded greater transient drops in blood pressure. Interestingly, the intrinsic rates that were mostly achieved by patients upon tilt were less than 60 bpm. See, Dr. med. Volker Schibgilla, "Influence of Artificial Cardiac Pacing on Cardiovascular Regulation of Pacemaker Patients: Significance and Therapeutic Implications", Medical Clinic II (Cardiology) with Teaching Hospital of the University of Erlangen-Nuremberg (Director: Prof. Dr. med. K. Bachmann), Habilitation Thesis of the Faculty of Medicine of the Friedrich Alexander University Erlangen-Nuremberg, 1997.

Research such as the Shibgilla report continues to fuel ongoing needs for improved techniques aimed at reducing the transient blood pressure drop upon orthostasis.

SUMMARY

An implantable cardiac device is programmed to promote intrinsic rhythm of a patient's heart to alleviate orthostatic hypotension. In one implementation, the cardiac device is set in a reduced rate mode while the patient is in a less upright position, such as when resting in a supine position. The reduced rate mode promotes intrinsic rhythm of the patient's heart by supporting a reduced pacing rate below the non-rest base rate. If the patient is in intrinsic rhythm when transitioning to a more upright position, the cardiac device disables administration of an increased pacing rate for a programmed duration. In this manner, the patient will experience a more natural variation in heart rate during transition from the less upright posture to the more upright posture (e.g., from supine to sitting or standing). This may allow a more natural vasoconstrictive response, leading to the reduced blood pressure drop. On the other hand, if the patient is being paced during the transition, the cardiac device may immediately administer an increased base rate or trigger an orthostatic response algorithm.

DETAILED DESCRIPTION

Overview

The following discussion describes an implantable cardiac device that promotes intrinsic rhythm of a patient's heart as a way to combat orthostatic hypotension. It is believed that by virtue of being in intrinsic rhythm, even though slow, the natural variation in rate and/or the (chronotropic) increase in heart rate during a postural change (impaired or not) will allow for a more natural vasoconstrictive response, leading to reduced blood pressure drop. The transient blood pressure drop upon orthostatic stress, such as standing, correlates positively with consequent symptoms of orthostasis, such as dizziness and/or lightheadedness. Because of this correlation, there is reason to believe that reducing the transient blood pressure drop upon orthostasis may also mitigate its symptoms, which afflict a significant percentage of pacemaker patients.

The implantable cardiac device is programmed to detect when a resting patient experiences a condition of non-rest, such as when the patient begins to sit up or stand after lying down for a prolonged period. If the patient's heart is being paced, the device may increase the pacing rate immediately through a preprogrammed orthostatic response algorithm. However, if the patient's heart is in intrinsic rhythm, the device disables any increased pacing rate for a programmed duration, such as 5 to 120 seconds, to allow a more natural vasoconstrictive response.

Implantable cardiac devices are commonly characterized as a miniature computing device that is implanted into the body of a patient to monitor, regulate, and/or correct heart activity. Such devices include implantable cardiac stimulation devices (e.g., implantable cardiac pacemakers, implantable defibrillators, cardiac rhythm management devices) that apply stimulation therapy to the heart and implantable cardiac monitors that monitor and record heart activity for diagnostic purposes. The following discussion describes first an exemplary cardiac device and then a mode of operation in which the device promotes intrinsic rhythm as a response to orthostatic hypotension.

Implantable Cardiac System

Figure 1:
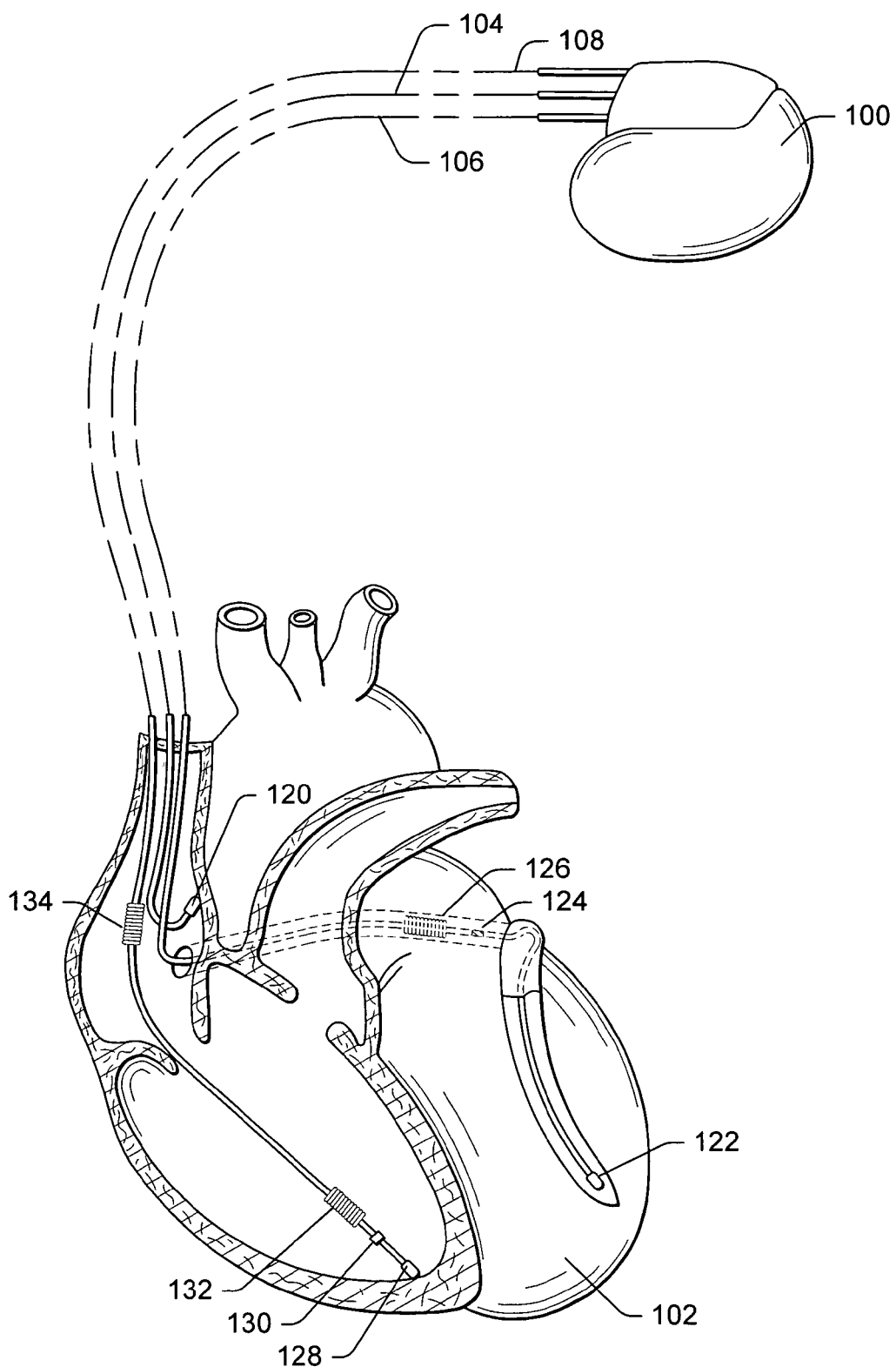
FIG. 1 is a diagrammatic illustration of an implantable cardiac device in electrical communication with a patient's heart for multi-chamber sensing and delivery of multi-chamber stimulation and shock therapy.

FIG. 1 shows an exemplary implantable cardiac device 100 in electrical communication with a patient's heart 102 for monitoring heart activity and/or delivering stimulation therapy, such as pacing therapies. Three leads—a right atrial lead 104, a coronary sinus lead 106, and a right ventricular lead 108—interconnect the device 100 with the patient's heart 102 to support multi-chamber detection and stimulation therapy.

The right atrial lead 104 supports an atrial tip electrode 120, which typically is implanted in the patient's right atrial appendage. The right atrial lead 104 enables the device to sense atrial cardiac signals and apply pacing therapy to the right atrial chamber.

The coronary sinus lead 106 positions a left ventricular tip electrode 122 adjacent to the left ventricle and/or additional electrode(s) adjacent to the left atrium, such as a left atrial ring electrode 124 and a left atrial coil electrode 126. The coronary sinus lead 106 enables the device 100 to sense left atrial and ventricular cardiac signals and administer left chamber pacing therapy. In the illustrated arrangement, the left ventricular tip electrode 122 is used to sense atrial and ventricular cardiac signals and deliver left ventricular pacing therapy. The left atrial ring electrode 124 is employed for applying left atrial pacing therapy, and the left atrial coil electrode 126 is used for shocking therapy.

The right ventricular lead 108 is electrically coupled to a right ventricular tip electrode 128, a right ventricular ring electrode 130, a right ventricular (RV) coil electrode 132, and an SVC coil electrode 134. Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of receiving cardiac signals, and delivering stimulation in the form of pacing and shock therapy to the right ventricle.

Figure 2:
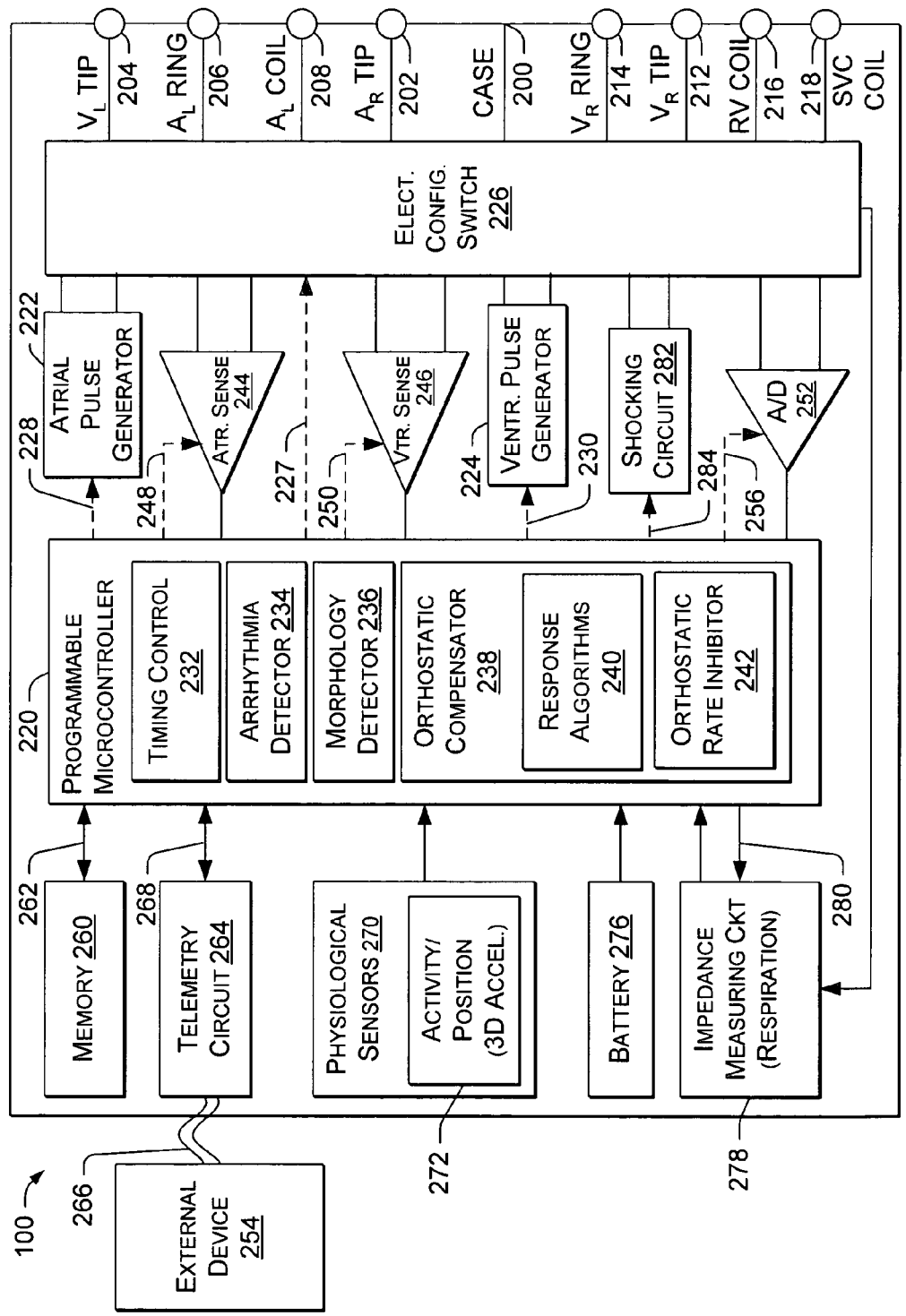
FIG. 2 is a functional block diagram of the multi-chamber implantable cardiac device.

FIG. 2 shows an exemplary, simplified block diagram depicting various components of the implantable cardiac device 100. The components are housed in housing 200, which is often referred to as the "can", "case", "encasing", or "case electrode". Housing 200 may be programmably selected as a return electrode for unipolar modes or in combination with one or more of the coil electrodes 126, 132 and 134 for shocking purposes. Housing 200 further includes a connector (not shown) having a plurality of terminals 202, 204, 206, 208, 212, 214, 216, and 218 (shown schematically and, for convenience, the names of the electrodes to which they are connected are shown next to the terminals), including:

a right atrial tip terminal (AR TIP) 202 for atrial tip electrode 120;

a left ventricular tip terminal (VL TIP) 204 for left ventricular tip electrode 122;

a left atrial ring terminal (AL RING) 206 for left atrial ring electrode 124;

a left atrial shocking terminal (AL COIL) 208 for left atrial coil electrode 126;

a right ventricular tip terminal (VR TIP) 212 for right ventricular tip electrode 128;

a right ventricular ring terminal (VR RING) 214 for right ventricular ring electrode 130;

a right ventricular shocking terminal (RV COIL) 216 for RV coil electrode 132; and an SVC shocking terminal (SVC COIL) 218 for SVC coil electrode 134.

The implantable cardiac device 100 includes a programmable microcontroller 220 that controls various operations, including cardiac monitoring and stimulation therapy. Microcontroller 220 includes a microprocessor (or equivalent control circuitry), RAM and/or ROM memory, logic and timing circuitry, state machine circuitry, and I/O circuitry.

Device 100 further includes an atrial pulse generator 222 and a ventricular pulse generator 224 that generate pacing stimulation pulses for delivery by the right atrial lead 104, the coronary sinus lead 106, and/or the right ventricular lead 108 via an electrode configuration switch 226. The switch 226 includes multiple switches for connecting the desired electrodes to the appropriate I/O circuits, thereby providing complete electrode programmability. Accordingly, switch 226, in response to a control signal 227 from the microcontroller 220, determines the polarity of the stimulation pulses (e.g., unipolar, bipolar, combipolar, etc.) by selectively closing the appropriate combination of switches. To provide stimulation therapy in each of the four chambers of the heart, the atrial and ventricular pulse generators 222 and 224 may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

Microcontroller 220 is illustrated as including timing control circuitry 232 to control the timing of the stimulation pulses (e.g., pacing rate, atrio-ventricular (AV) delay, atrial interconduction (A—A) delay, or ventricular interconduction (V—V) delay, etc.). The timing control circuitry may also be used for the timing of refractory periods, blanking intervals, noise detection windows, evoked response windows, alert intervals, marker channel timing, and so on.

Microcontroller 220 is equipped with an arrhythmia detector 234 and a morphology detector 236 to evaluate various data collected by the cardiac device in an effort to detect arrhythmia and morphological events. An orthostatic compensator 238 is also implemented by the microcontroller 220 to detect when a patient experiences orthostatic hypotension caused by transition from a less upright posture to a comparatively more upright posture. One example postural change is when a patient moves from a supine position in a rest state (e.g., sleeping in bed) to an upright position in a non-rest state (e.g., sitting or standing up). In response to the detected postural change, the orthostatic compensator 238 administers one or more pacing therapies to reduce any effects of orthostatic hypotension.

The orthostatic compensator 238 includes one or more response algorithms 240 that may be invoked to combat orthostatic hypotension or any symptoms indicative of orthostatic hypotension. If the patient's heart is not in intrinsic rhythm (e.g., it is being paced) when the transition is detected, the orthostatic compensator 238 applies one of the response algorithms 240 to counter the effects of orthostatic hypotension. The algorithms 240 maybe programmed to administer increased pacing, decreased pacing, or a combination of both. Such pacing changes may be applied in many different ways, including step-wise changes.

On the other hand, if the patient's heart is in intrinsic rhythm when the patient transitions from a less upright posture to a more upright posture, the orthostatic compensator 238 invokes an orthostatic rate inhibitor 242 to temporarily disable any responsive pacing measures (e.g., increased or decreased pacing) for a programmable duration of time. One example duration is 5–120 seconds. After this duration expires, the compensator 238 can then change the pacing rate, such has increasing the pacing rate to the base rate or triggering one of the response algorithms 240.

The components 234–238 may be implemented in hardware as part of the microcontroller 220, or as software/firmware instructions programmed into the device and executed on the microcontroller 220 during certain modes of operation. These components 234–238 may further be implemented independent from the microcontroller 220. Although not shown, the microcontroller 220 may further include other dedicated circuitry and/or firmware/software components that assist in monitoring various conditions of the patient's heart and managing pacing therapies.

Atrial sensing circuits 244 and ventricular sensing circuits 246 may also be selectively coupled to the right atrial lead 104, coronary sinus lead 106, and the right ventricular lead 108, through the switch 226 to detect the presence of cardiac activity in each of the four chambers of the heart. The sensing circuits 244 and 246 may include dedicated sense amplifiers, multiplexed amplifiers, or shared amplifiers. Switch 226 determines the "sensing polarity" of the cardiac signal by selectively closing the appropriate switches. In this way, the clinician may program the sensing polarity independent of the stimulation polarity. Each sensing circuit 244 and 246 may employ one or more low power, precision amplifiers with programmable gain and/or automatic gain control, band pass filtering, and threshold detection circuitry to selectively sense the cardiac signal of interest. The automatic gain control enables the device 100 to sense low amplitude signal characteristics of atrial or ventricular fibrillation.

The outputs of the atrial and ventricular sensing circuits 244 and 246 are connected to the microcontroller 220 which, in turn, is able to trigger or inhibit the atrial and ventricular pulse generators 222 and 224 in response to the absence or presence of cardiac activity in the appropriate chambers of the heart. The sensing circuits 244 and 246 receive control signals from the microcontroller 220 over signal lines 248 and 250 for purposes of controlling the gain, threshold, polarization charge removal circuitry (not shown), and the timing of any blocking circuitry (not shown) coupled to the inputs of the sensing circuits.

Cardiac signals are supplied to an analog-to-digital (A/D) data acquisition system 252, which is configured to acquire intracardiac electrogram (IEGM) signals, convert the raw analog data into a digital signal, and store the digital signals for processing and/or for telemetric transmission to an external device 254. The data acquisition system 252 is coupled to the right atrial lead 104, the coronary sinus lead 106, and the right ventricular lead 108 through the switch 226 to sample cardiac signals across any pair of desired electrodes.

The data acquisition system 252 is coupled to the microcontroller 220, or other detection circuitry, to assist in detecting an evoked response from the heart 102 in response to an applied stimulus, which is otherwise known as detecting "capture". Capture occurs when an electrical stimulus applied to the heart is of sufficient energy to depolarize the cardiac tissue, thereby causing the heart muscle to contract. The microcontroller 220 detects a depolarization signal during a window following a stimulation pulse, the presence of which indicates that capture has occurred. The microcontroller 220 enables capture detection by triggering the ventricular pulse generator 224 to generate a stimulation pulse, starting a capture detection window using the timing control circuitry 232 within the microcontroller 220, and enabling the data acquisition system 252 via control signal 256 to sample the cardiac signal that falls in the capture detection window and, based on the amplitude, determines if capture has occurred.

Capture detection may occur on a beat-by-beat basis or on a sampled basis. A capture threshold search can desirably be performed once a day during at least the acute phase (e.g., the first 30 days) and less frequently thereafter. A capture threshold search would begin at a desired starting point (either a high energy level or the level at which capture is currently occurring) and decrease the energy level until capture is lost. The value at which capture is lost is known as the capture threshold. Thereafter, a safety margin is added to the capture threshold.

The microcontroller 220 is further coupled to a memory 260 by a suitable data/address bus 262. The programmable operating parameters used by the microcontroller 220 are stored in memory 260 and used to customize the operation of the device 100 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 102 within each respective tier of therapy.

The operating parameters of the implantable device 100 may be non-invasively programmed into the memory 260 through a telemetry circuit 264 in telemetric communication via communication link 266 with the external device 254. The external device 254 may be implemented in many ways, including as a programmer, a transtelephonic transceiver, or a diagnostic system analyzer. The microcontroller 220 activates the telemetry circuit 264 with a control signal 268. The telemetry circuit 264 allows intracardiac electrograms and status information relating to the operation of the device 100 (as contained in the microcontroller 220 or memory 260) to be sent to the external device 254 through an established communication link 266.

The implantable cardiac device 100 can further include one or more physiologic sensors 270. Such sensors are commonly referred to as "rate-responsive" sensors because they are typically used to adjust pacing stimulation rates according to the exercise state of the patient. However, the physiological sensor(s) 270 may further be used to detect changes in cardiac output, changes in the physiological condition of the heart, diurnal changes in activity (e.g., detecting sleep and wake states), or respiration activity (e.g., minute ventilation). The microcontroller 220 responds to changes sensed by the sensor(s) 270 by adjusting various pacing parameters (such as rate, AV Delay, V—V Delay, etc.) at which the atrial and ventricular pulse generators 222 and 224 generate stimulation pulses. While shown as being included within the device 100, the physiologic sensor(s) 270 may also be external to the device 100, yet still be implanted within or carried by the patient. Examples of physiologic sensors that may be implemented in device 100 include sensors that, for example, sense respiration activities, O2 saturation, evoked response, pH of blood, and so forth.

In the illustrated implementation, the physiological sensors 270 include sensors for detecting patient activity and/or position changes. Any sensor capable of sensing such conditions, either directly or indirectly, may be used. In particular, the physiological sensors 270 include an activity/position sensor 272 to detect patient movement and/or changes from one position to another. The sensor 272 may be implemented in many ways, including as an accelerometer. The accelerometer may be configured as a one-dimensional (1D) accelerometer to sense acceleration in a single dimension, or a three-dimensional (3D) accelerometer to sense acceleration in three dimensions.

In one configuration, the accelerometer output signal is bandpass-filtered, rectified, and integrated at regular timed intervals. The processed accelerometer signal is used as a raw activity signal. The device derives an activity measurement based on the raw activity signal at intervals timed according to the cardiac cycle. The activity signal alone can be used to indicate whether a patient is active or resting. The activity measurement can further be used to determine an activity variance parameter. A large activity variance signal is indicative of a prolonged exercise state. Low activity and activity variance signals are indicative of a prolonged resting state. The activity variance can be monitored diurnally to detect the low variance in the measurement corresponding to the sleep state. For a complete description of the activity variance sensor, the reader is directed to U.S. Pat. No. 5,476,483 (Bornzin et al.), issued Dec. 19, 1995, which is hereby incorporated by reference.

The activity signals generated by the sensors 270 are passed to the microcontroller 220 for analysis by the orthostatic compensator 238. Such signals can be used to determine whether the patient is changing postures, such as from a supine position to a vertical position (e.g., when standing after lying in a horizontal position). If such movement is confirmed, the orthostatic compensator can determine an appropriate response to reduce the effects of orthostatic hypotension which may result from the posture change.

The implantable cardiac device 100 additionally includes a battery 276 to supply operating power to various components shown in FIG. 2. The battery 276 is capable of operating at low current drains for long periods of time (e.g., less than 10 μA), and is capable of providing high-current pulses (for capacitor charging) when the patient requires a shock pulse (e.g., in excess of 2 A, at voltages above 2 V, for periods of 10 seconds or more). The battery 276 also desirably has a predictable discharge characteristic so that an elective replacement time can be detected. As one example, the device 100 employs lithium/silver vanadium oxide batteries.

The device 100 can further include magnet detection circuitry (not shown), coupled to the microcontroller 220, to detect when a magnet is placed over the stimulation device 100. A magnet may be used by a clinician to perform various test functions of the stimulation device 100 and/or to signal the microcontroller 220 that the external programmer 254 is in place to receive or transmit data to the microcontroller 220 through the telemetry circuits 264.

The device 100 further includes an impedance measuring circuit 278 that is enabled by the microcontroller 220 via a control signal 280. The impedance measuring circuit 278 is used for many things, including: lead impedance surveillance during the acute and chronic phases for proper lead positioning or dislodgement; detecting operable electrodes and automatically switching to an operable pair if dislodgement occurs; measuring thoracic impedance for determining shock thresholds; detecting when the device has been implanted; measuring stroke volume; and detecting the opening of heart valves; and so forth. In particular relevance to our ongoing discussion, the impedance measuring circuit 278 can be used to measure respiration-related parameters, such as respiration rate, minute ventilation, respiration signal amplitude, and tidal volume. The impedance measuring circuit 278 is coupled to the switch 226 so that any desired electrode may be used.

The device 100 can be operated as an implantable cardioverter/defibrillator (ICD) device, which detects the occurrence of an arrhythmia and automatically applies an appropriate electrical shock therapy to the heart aimed at terminating the detected arrhythmia. To this end, the microcontroller 220 further controls a shocking circuit 282 by way of a control signal 284. The shocking circuit 282 generates shocking pulses of low (e.g., up to 0.5 Joules), moderate (e.g., 0.5 to 10 Joules), or high energy (e.g., 11 to 40 Joules), as controlled by the microcontroller 220. Such shocking pulses are applied to the patient's heart 102 through at least two shocking electrodes selected, for example, from the left atrial coil electrode 126, the RV coil electrode 132, and/or the SVC coil electrode 134. As noted above, the housing 200 may act as an active electrode in combination with the RV electrode 132, or as part of a split electrical vector using the SVC coil electrode 134 or the left atrial coil electrode 126 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 Joules), delivered asynchronously (since R-waves may be too disorganized), and pertaining exclusively to the treatment of fibrillation. Accordingly, the microcontroller 220 is capable of controlling the synchronous or asynchronous delivery of the shocking pulses.

Process

Figure 3:
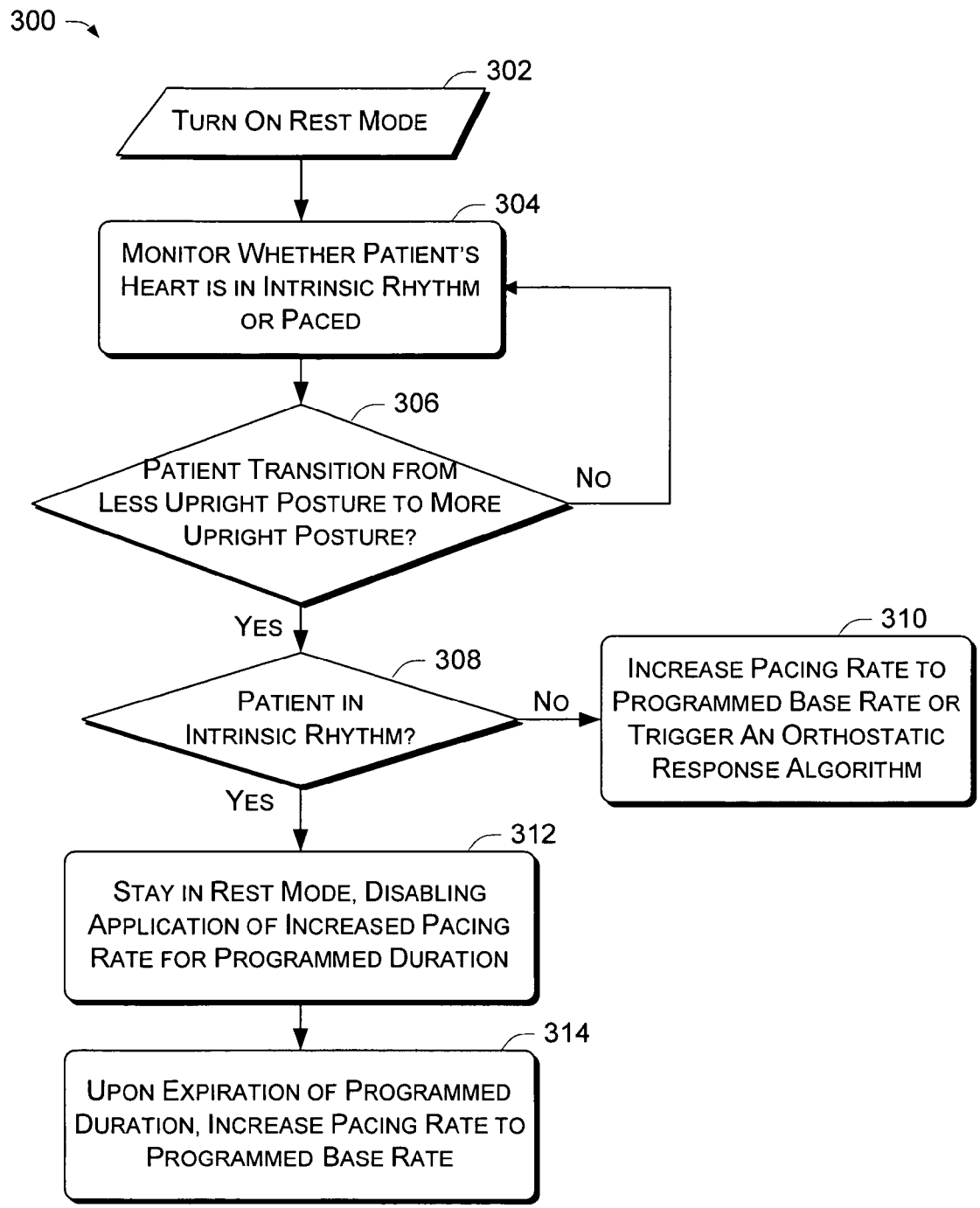
FIG. 3 is a flow diagram of a process for promoting intrinsic rhythm of a patient's heart to alleviate orthostatic hypotension.

FIG. 3 shows a process 300 for promoting intrinsic rhythm to alleviate orthostatic hypotension. This process 300 may be implemented in connection with any suitably configured device, although it will be described as being executed by the implantable cardiac device 100 of FIGS. 1 and 2. In the flow diagram of FIG. 3, the operations are summarized in individual blocks. The operations may be performed in hardware and/or as machine-readable instructions (software or firmware) that can be executed by a processor.

As mentioned above, patients typically experience orthostatic hypotension when they get up from a prolonged rest. Accordingly, at block 302, the implantable cardiac device 100 initially determines when the patient is at rest and activates the Rest Mode functionality to support reduced cardiac pacing (e.g., 40 bpm) below a non-rest base rate. There are many ways to detect when a patient is resting. One approach is to monitor patient activity, or activity variance, via the activity sensor 272 and confirm that a patient is at rest when the patient has been inactive for a predetermined amount of time. Another approach is to monitor respiration changes. Another technique is to detect patient position, and whether the patient is in a supine position, rather than upright. Other indicia of rest may also be utilized.

It is further noted that the Rest Mode may be activated even when a patient is not sleeping. Rather, "Rest Mode" represents a reduced pacing mode where the cardiac device 100 paces at a reduced rate below the non-rest base rate.

At block 304, the device 100 monitors whether the patient's heart is in intrinsic rhythm or is being paced at the programmed rate of Rest Mode. Intrinsic rhythm is achieved when the patient's heart beats at a natural cadence ahead of when pacing pulses would be applied in Rest Mode, thereby inhibiting application of the pulses when a beat occurs. Alternatively, the patient's heart may be paced while in Rest Mode according to the reduced pacing rate. The device can perform this monitoring on a beat-by-beat basis, or in a less frequent manner.

At block 306, the cardiac device 100 detects when the patient transitions from a less upright posture to a more upright posture. One example of where this occurs is when a patient sits or stands up after lying down. Another example is where a patient simply moves from a reclined position to a less reclined position, such as when leaning forwards in a reclining chair. Such a condition can be referred to as an "Out of Rest Mode" condition.

The postural change can be detected in a number of ways. One approach is to monitor patient activity via the activity sensor 272 and confirm that the patient has once again become active, indicating that the patient is no longer lying still. Another approach is to detect an increase in respiration. Another technique is to use the accelerometer to detect whether the patient's position has changed from a supine position to an upright or tilt position. Other indicia of postural change may also be utilized.

If there is no postural change (i.e., the "No" branch from block 306), the device continues to monitor for intrinsic rhythm and future conditions indicative of posture change. Once the patient changes postures from a less upright posture to a more upright posture (i.e., the "Yes" branch from block 306), the device 100 determines whether the patient's heart is in intrinsic rhythm (block 308).

If the patient's heart is not in intrinsic rhythm (i.e., the "No" branch from block 308), the device 100 increases the pacing rate to a programmed base rate and/or triggers one of the orthostatic response algorithms 240 to combat any onset of orthostatic hypotension (block 310). For a patient with a rest rate of 40 ppm, an example programmed base rate might be 60–70 ppm. Orthostatic response algorithms may involve increasing the pacing rate even more. For example, a response algorithm might direct a device to pace at 80–90 ppm for a predetermined time period, and then decrease over time in a programmed manner (e.g., stepwise), to the base rate. The elevation in heart rate may occur rapidly (e.g., increasing 20–40 ppm in two to three heart beats). Alternatively, orthostatic response algorithms may be designed to include a decrease in pacing rate.

If the patient's heart is in intrinsic rhythm (i.e., the "Yes" branch from block 308), the device 100 remains in Rest Mode for a programmed duration (block 312). That is, the device 100 continues at the reduced pacing rate (e.g., 40 ppm) and disables any responsive pacing rate (increased or decreased) for a predetermined period of time to allow for a more natural response to orthostatic stress caused by the postural change. One example duration is 5 to 120 seconds. Disabling any increase in pacing rate facilitates a more natural vasoconstrictive response, leading to a reduced blood pressure drop, thereby countering the effects of orthostatic hypotension.

Upon expiration of the programmed period, the device 100 increases the pacing rate to a programmed pacing rate (block 314). This increase in pacing rate may be performed over a programmed transition duration.

The operations described in blocks 308–314 can be implemented, for example, by the orthostatic compensator module 238 based on feedback from the sensing circuits and analysis by the microcontroller as to whether the patient's heart is intrinsic or paced. If not in intrinsic rhythm, the orthostatic compensator module 238 directs the device to increase the pacing rate to a programmed base rate and/or select one of the orthostatic response algorithms 240. Conversely, if the heart is in intrinsic rhythm, the orthostatic compensator module 238 invokes the orthostatic rate inhibitor to disable any pacing responses, thereby leaving the device in Rest Mode for a programmed duration.

CONCLUSION

The foregoing discussion describes promotion of intrinsic rhythm of a patient's heart to alleviate orthostatic hypotension. Although the invention has been described in language specific to structural features and/or methodological acts, it is to be understood that the subject matter defined in the appended claims is not necessarily limited to the specific features or acts described. Rather, the specific features and acts are disclosed as exemplary forms of implementing the claimed invention.

What is claimed is:

1. An implantable cardiac device comprising:
   circuitry to sense whether a patient is in intrinsic rhythm when transitioning from a less upright posture to a more upright posture; and
   a processor to promote vasoconstrictive response of the patient's heart by:
   (i) in an event that the circuitry senses the patient is not in intrinsic rhythm, applying increased pacing to counter effects of orthostatic hypotension caused by the transition from the less upright posture to the more upright posture; and
   (ii) in an event that the circuitry senses the patient is in intrinsic rhythm, disabling increased pacing for a programmed duration, wherein the programmed duration is approximately 5–120 seconds.

2. An implantable cardiac device as recited in claim 1, wherein the circuitry comprises at least one of an activity sensor, an accelerometer, and a respiration sensor to sense the condition indicative of non-reset.

3. An implantable cardiac device as recited in claim 1, wherein the increased pacing is applied according to an orthostatic response algorithm.

4. An implantable cardiac device as recited in claim 1, wherein the processor applies increased pacing after the programmed duration expires.

5. An implantable cardiac device comprising:
   detection means for detecting whether a patient is in intrinsic rhythm when transitioning from a first posture to a second posture, where the second posture is more upright than the first posture; and
   responsive to the transition in posture, compensation means for temporarily disabling, for a programmed duration, application of increased pacing to counter effects of orthostatic hypotension if the patient is in intrinsic rhythm and subsequently applying, after expiration of the programmed duration, a pacing therapy;
   wherein the programmed duration is approximately 5–120 seconds.

6. An implantable cardiac device as recited in claim 5, wherein the compensation means applies a pacing therapy that includes increased pacing.

7. An implantable cardiac device as recited in claim 5, wherein the compensation means applies a pacing therapy that includes decreased pacing.

8. An implantable cardiac device as recited in claim 5, wherein the compensation means applies increased pacing without delay if the patient is not in intrinsic rhythm.

9. An implantable cardiac device having a memory and a processor, the cardiac device being programmed to perform tasks comprising countering orthostatic hypotension by disabling, for a programmed duration, application of increased pacing to a patient who is in intrinsic rhythm when transitioning from a first posture to a second posture that is more upright than the first posture, the programmed duration being approximately 5–120 seconds.

10. An implantable and programmable cardiac device as recited in claim 9, further programmed to perform tasks comprising subsequently applying the increased pacing after the programmed duration lapses.

11. A method implemented by an implantable cardiac device, comprising:
   sensing when a patient transitions from a less upright posture to a more upright posture; and
   disabling increased pacing responsive to the transition if the patient's heart is in intrinsic rhythm to promote a vasoconstrictive response, wherein said disabling is for a programmed duration, and wherein the programmed duration is approximately 5–120 seconds.

12. A method as recited in claim 11, wherein the sensing comprises monitoring at least one of a respiration-related parameter, an activity variance, or a position-related parameter.

13. A method as recited in claim 11, wherein the sensing comprises determining when the patient, who is at rest, exhibits indicia of non-rest.

14. A method as recited in claim 11, further comprising administering increased pacing after expiration of the programmed duration.

15. A method as recited in claim 11, further comprising administering decreased pacing after expiration of the programmed duration.

16. A method comprising:
   when a patient is at rest, determining whether the patient's heart is in intrinsic rhythm;
   detecting a condition indicative of non-rest;
   if the patient's heart is not in intrinsic rhythm, administering increased pacing upon detection of the condition to counter effects of orthostatic hypotension; and
   if the patient's heart is in intrinsic rhythm, disabling administration of the increased pacing for a programmed duration to promote vasoconstrictive response of the patient's heart, wherein the programmed duration is approximately 5–120 seconds.

17. A method as recited in claim 16, wherein the detecting comprises monitoring the patient's position.

18. A method as recited in claim 16, wherein the detecting comprises monitoring patient activity.

19. A method as recited in claim 16, further comprising subsequently increasing pacing after the programmed duration expires.

* * * * *